(12) United States Patent
Eslahi et al.

(10) Patent No.: US 9,695,455 B2
(45) Date of Patent: Jul. 4, 2017

(54) METHOD FOR SYNTHESIZING PROTEIN NANOPARTICLES USING WASTE CHICKEN FEATHERS

(71) Applicants: Niloofar Eslahi, Tehran (IR); Fatemeh Dadashian, Tehran (IR); Nahid Hemmatinejad, Tehran (IR)

(72) Inventors: Niloofar Eslahi, Tehran (IR); Fatemeh Dadashian, Tehran (IR); Nahid Hemmatinejad, Tehran (IR)

( * ) Notice: Subject to any disclaimer, the term of this patent is extended or adjusted under 35 U.S.C. 154(b) by 138 days.

(21) Appl. No.: 14/641,460

(22) Filed: Mar. 9, 2015

(65) Prior Publication Data

US 2016/0265020 A1    Sep. 15, 2016

(51) Int. Cl.
*A61K 9/51* (2006.01)
*C12P 21/06* (2006.01)

(52) U.S. Cl.
CPC ............ *C12P 21/06* (2013.01); *A61K 9/5169* (2013.01)

(58) Field of Classification Search
None
See application file for complete search history.

(56) References Cited

U.S. PATENT DOCUMENTS

| 4,908,220 A * | 3/1990 | Shih .......................... A23J 1/10 426/61 |
| 2010/0196302 A1* | 8/2010 | Vermelho ............... C12P 21/06 514/1.1 |

FOREIGN PATENT DOCUMENTS

CN    102826922    * 12/2012

OTHER PUBLICATIONS

Eslahi N. et al. An Investigation on Keratin Extraction from Wool and Feather Waste by Enzymatic Hydrolysis. Preparative Biochemistry & Biotechnology 43(7)624-648 2013.*
Eslahi N. et al. From Feather Waste to Valuable Nanoparticles. Particulate Science and Technology 32(3)242-250, May 4, 2014.*
Estevez-Martinez Y. et al. Grafting of Multiwalled Carbon Nanotubes with Chicken Feather Keratin. J of Nanomaterials ID 702157, 2013, 9 pages.*

* cited by examiner

*Primary Examiner* — Ralph Gitomer
(74) *Attorney, Agent, or Firm* — Barry Choobin; Patent 360

(57) ABSTRACT

A method of producing protein nanoparticles from waste chicken feathers by enzymatic hydrolysis followed by ultrasonic treatment is disclosed. The process includes pretreatment of the chicken feathers. Then feather fibers are hydrolyzed enzymatically. The effects of enzyme concentration, hydrolysis time, and substrate concentration on particle mean size are analyzed to optimize the best condition in order to attain the smallest particles by a Box-Behnken Design. A minimum particle size is obtained by using 5 g/l feather and 3.6% enzyme with a hydrolysis time of 243 h. The hydrolyzed particles are then subjected to ultrasonic treatment to produce nanoparticles. The produced protein particles have high potential to be used in nanocomposites and adsorbents.

12 Claims, 11 Drawing Sheets

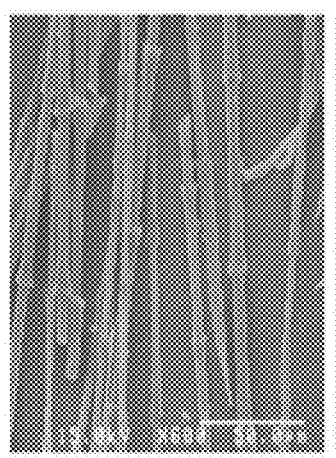  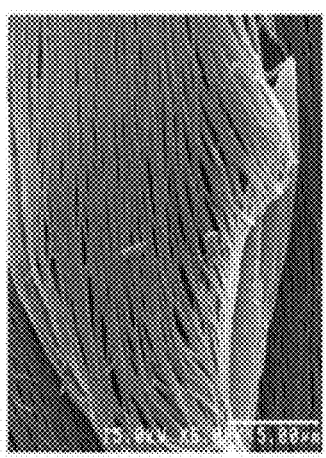
FIG.3A  FIG.3B  FIG.3C
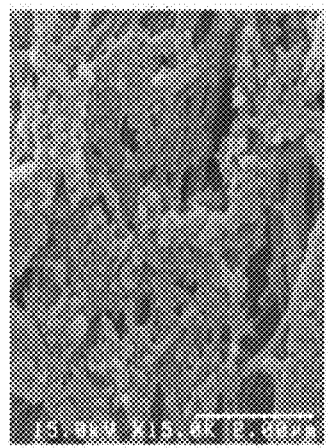 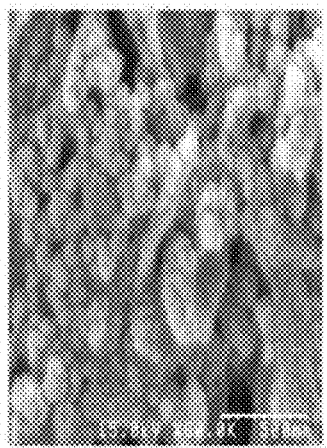 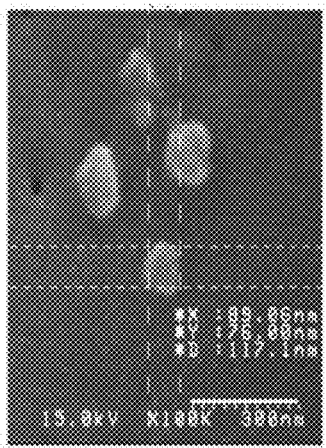
FIG.3D  FIG.3E  FIG.3F

METHOD FOR SYNTHESIZING PROTEIN NANOPARTICLES USING WASTE CHICKEN FEATHERS

BACKGROUND

Technical Field

The embodiments herein generally relate to the field of nanotechnology. The embodiment herein particularly relate to the synthesis of nanoparticles and particularly to protein nanoparticles. The embodiments herein more particularly relate to optimization of an enzyme hydrolysis of feather fibers using RSM for the synthesis of protein nanoparticles from waste chicken feathers.

Description of the Related Art

Nanoparticles are particles between 1 and 100 nanometers in size. In nanotechnology a particle is defined as a small object that behaves as a whole unit with respect to its transport and properties. The nanoparticles are further classified according to diameter. The ultrafine particles have a size of 1-100 nm and the coarse nanoparticles cover a range between 2500 and 10,000 nm. The fine particles are sized 100 and 2500 nanometers.

The methods for synthesizing nanoparticles are categorized into two broad classes: A) Top down approach involving attrition or milling and B) Bottom up approach involving pyrolysis, inert gas condensation, solvothermal reaction, sol-gel fabrication, and structured media method.

The methods of synthesizing the metal nanoparticles from these methods are costly. Further use of metals such as silver and gold makes the nanoparticles more costly. Also the steps involved in the top down approach and the bottom up approach involves many chemical reactions and also requires energy.

The metal nanoparticles also have many adverse affects. It has been reported that metal nanoparticles are small enough to be absorbed by the skin and cause irritation. Further the nanoparticles (synthetic or metal) speed up the metabolic reactions in unpredictable ways. The silver nanoparticles are known to kill bacteria. Further silver nanoparticles also kill useful bacteria. The zinc oxide and cerium oxide nanoparticles have been shown to affect soybean plant growth. Also cerium oxide has been shown to completely inhibit the plants ability to fix nitrogen in the mammalian cells grown under laboratory conditions.

Feathers are one of the epidermal growths that form the distinctive outer covering or plumage on birds. Feathers are considered most complex integumentary structures found in vertebrates. The feathers cover most parts of the body of birds; they arise only from certain well defined tracts on the skin. Feathers aid in flight, thermal insulation, water proofing and coloration that helps in communication and protection.

Feathers are complex integumentary appendages found in vertebrates and are formed in tiny follicles in the epidermis or outer skin layer, that produce keratin proteins. The β-keratins in feathers are composed of protein strands. The protein strands are hydrogen bonded into 3-pleated sheets which are then twisted and cross-linked by disulfide bridges into structures even tougher than α-keratin.

Feathers represent from 5% to 7% of the body weight of chickens. These important by-products of the poultry industry are produced in millions of tons annually throughout the world. Chicken feathers are approximately half feather fiber (barbs) and half quill (rachis) by weight. The quill is the stiff central core, to which the soft and interlocking fibers are branched. Both feather fiber and quill are made of keratin (about 90% by weight). The keratin is an insoluble and highly durable protein found in hair, hoofs and horns of animals. Fibers from chicken feathers have several distinctive features such as: surface toughness, flexibility, high length to diameter ratio, hydrophobicity and an highly organized morphology characterized by its complex hierarchical structure. Further the protein fibers are effectively self-sustainable, biodegradable and continuously renewable due to their natural biopolymer origin.

Despite the unique properties, feathers are largely disposed of by incineration which leads to environmental problems. Recycling feathers, which are source of biopolymers have been the objective of many researches because of their high protein content, biodegradability and biocompatibility.

The protein particles from the feathers keep the original properties of the material without destroying the microstructure, it has been widely applied in modern industries. Some researchers have tried to produce feather particles by different methods such as mechanical attrition and regeneration from keratin solution through crushing and obtaining film, spray drying or electro-spraying techniques. The recovered keratin from feather in particles form has applications in cosmetics, composites, and food and drug delivery. The keratin is used in the aforesaid application because of the properties such as biocompatibility, biodegradability and moisture absorption. However long time of dialysis, high production costs, safety and environmental problems constitute the main shortcomings of dissolution routes. Mechanical attrition which involves chopping and crushing the fibers with suitable milling machines avoid these problems, but this method has high energy consumption.

Intensive research demonstrates that the efficiency of the enzymatic hydrolysis depends on several parameters such as enzyme concentration, reaction time, substrate concentration, addition of surfactant. These factors often interact with one another therefore, optimization of the enzymatic hydrolysis process is important in improving the performance of the procedure or method. Unlike conventional optimization, statistical optimization methods take into account the interactions of variables in generating process responses. Response surface methodology (RSM) is an efficient mathematical approach for optimizing complex processes. Further RSM is an efficient method for optimizing hydrolysis process which generates an empirical model for evaluation of the relationship of a set of controlled experimental factors and the observed results. The RSM statistical technique is applied in different chemical and biochemical processes to analyze the effect of independent variables and optimize the process responses using appropriate values of the factors. The main advantage of RSM is the reduced number of experimental trials needed to evaluate multiple parameters and their interactions by establishing a mathematical model while keeping a high degree of statistical significance in the results. The RSM is used to optimize the enzymatic hydrolysis of various resources. In many trials the optimization of the parameters is based on hydrolysis yield for obtained protein hydrolysates.

Hence there is a need to synthesize protein nanoparticles from waste chicken feathers. Also there is a need to synthesize protein nanoparticles from chicken feathers using enzymatic hydrolysis method.

The above mentioned shortcomings, disadvantages and problems are addressed herein and which will be understood by reading and studying the following specification.

OBJECTIVES OF THE EMBODIMENTS

The primary objective of the embodiment herein is to synthesize nanoparticles from waste chicken feather by enzyme hydrolysis followed by ultrasonic treatment.

Another object of the embodiment herein is to examine the influence of enzyme concentration, substrate concentration and hydrolysis time on the particle size of the protein nanoparticles synthesized from waste chicken feather.

Yet another object of the embodiment herein is to optimize the process of synthesizing the protein nanoparticles from waste chicken feather by using Response Surface Methodology (RSM).

Yet another objective of the embodiment herein is to optimize the conditions in order to attain the smallest particles by a Box-Behnken Design (BBD) to synthesize the protein nanoparticles from waste chicken feathers.

Yet another objective of the embodiment herein is to synthesize the protein nanoparticles from waste chicken feather with enhanced crystallinity and thermal stability.

Yet another objective of the embodiment herein is to synthesize the protein nanoparticles from waste chicken feather which have high protein content, biodegradability and biocompatibility.

Yet another objective of the embodiment herein is to provide the particle size modeling of the hydrolyzed chicken feather by protease.

Yet another objective of the embodiment herein is to investigate the production of protein nanoparticles from waste chicken feather by enzymatic hydrolysis, having milder processing conditions thereby leaving no harmful by products.

These objects and the other advantages of the embodiments herein will become readily apparent from the following detailed description taken in conjunction with the accompanying drawings.

SUMMARY

The various embodiments herein provide protein nanoparticles synthesized from waste chicken feathers by enzyme hydrolysis followed by ultrasonic treatment. The present invention also examines the influence of enzyme concentration, substrate concentration and hydrolysis time on the particle size of the protein nanoparticles synthesized from waste chicken feather. Further the process of synthesizing the protein nanoparticles from waste chicken feather is optimized by using Response Surface Methodology (RSM). The process of synthesizing protein nanoparticles has milder processing conditions thereby leaving no harmful by products. The protein nanoparticles synthesized from waste chicken feather with enhanced crystallinity and thermal stability.

According to one embodiment herein, a method of synthesizing protein nanoparticles from waste chicken feathers, comprises the following steps of pretreating the plurality of waste chicken feathers, hydrolyzing the plurality of waste chicken feather fibers enzymatically, analyzing the effects of an enzyme concentration, a hydrolysis time and a substrate concentration and synthesizing the feather nanoparticles according to a particle shape, a particle size, crystallinity index and thermal stability characteristics.

According to one embodiment herein, the steps of pretreating the chicken feathers comprises washing the plurality of waste chicken feathers in an aqueous solution for 30 minutes at 60° C. The aqueous solution comprises 1 g/L of a non-ionic detergent and 1 weight % of sodium carbonate at liquid to fiber ratio of 40 ml/g. Further rinsing the chicken feathers and drying. The chicken feathers are subjected to a Soxhert extracting, where the chicken feathers are boiled in the petroleum ether for 12 hours to remove grease to obtain de-fattened feather fibers. The chicken feathers are boiled in petroleum ether at 40-60° C. The petroleum ether is evaporated. The chicken feathers are rinsed with distilled water for a plurality of times. The chicken feathers are dried at room temperature. The de-fattened feather fibers are cleaned. The cleaned and de-fattened feather fibers are separated from quill and the de-fattened fibers are chopped into short pieces.

According to one embodiment herein, the steps of hydrolyzing the chicken feathers enzymatically comprises incubating the feather fibers with savinase in a 10 ml borate buffer solution at 55° C. The borate buffer solution comprises 6 g/L of a sodium bisulfate and a 1 g/L sodium dodecyl sulfate (SDS). The sodium bisulfate is a reducing agent and the SDS is an anionic surfactant. The hydrolyzed feather fiber samples are scooped out at a plurality of processing intervals, and the plurality of processing intervals have mutually different time periods. The plurality of processing intervals is 3.

According to one embodiment herein, the enzyme savinase is deactivated by adding a solution of an acetic acid (1M). The acetic acid is added to reduce the pH to 4.5. The temperature is increased to 75° C. for 20 min. The enzyme and feather fiber solution is agitated at 300 rpm. The plurality of hydrolyzed feather samples are centrifuged at 8000 rpm for 5 min to separate the particles from residual solution. The supernatants are decanted from particle fraction after centrifugation. The particle fraction is repeatedly washed with deionized water. The particle fraction with deionized water is centrifuged at 8000 rpm; and drying the particle fraction.

According to one embodiment herein, the steps of analyzing the effects of an enzyme concentration, a hydrolysis time and a substrate concentration comprises acquiring the scooped out feather samples at the plurality of processing intervals. The enzyme concentration, the hydrolysis time and the substrate concentration are estimated in each sample acquired at the plurality of processing intervals. The estimated enzyme concentration, hydrolysis time and substrate concentration are substituted in each sample in a regression equation. The regression equation is fitted in a statistical model represented by a 15 run Box-Behnken Design (BBD) model to obtain an experimental data to optimize the enzyme concentration (%), the hydrolyzing time (h) and the substrate concentration (g/L). The experimental data is analyzed using a Design-Expert Software to yield a regression equation. The optimum parameter combinations of the enzyme concentration, the hydrolysis time and the substrate concentration are determined. The optimal values of the independent parameters of enzyme concentration, hydrolysis time and substrate concentration are obtained by solving the regression equation. The surface response and contour plots for the parameters of enzyme concentration, hydrolysis time and substrate concentration are analyzed. The optimal substrate concentration is found to be 5 g/L feather, the optimal enzyme concentration is found to be 3.6% and the optimal hydrolysis time is found to be 243 hours.

According to one embodiment herein, the steps of synthesizing the feather nanoparticles according to the particle shape, the particle size, crystallinity index and the thermal stability characteristics comprises suspending the centrifuged particle fraction in distilled water for determining a particle size distribution. The particle size distribution is determined by a particle size analyzer. The centrifuged particles are subjected to ultrasonic treatment for 15 min at 80% amplitude. The morphology of the chicken feather nanoparticles is evaluated with a scanning electronic microscope.

According to one embodiment herein, the nano particles are subjected to a sonication (ultrasonication), a surface morphology analysis, a particle size analysis, a FTIR spectroscopy, a XRD, and a thermal analysis for synthesizing the nano particles according to particle shape, size and thermal stability characteristics.

According to one embodiment herein, the nanoparticles are subjected to the sonication to reduce the particle size from 297 nm to 127 nm after sonication. 68.2% of the sonicated particles have a particle size of less than 100 nm. 25.3% of the sonicated particles have a particle size within a range of 100-120 nm. 1.5% of the sonicated particles have a particle size in the range of 120-140. 5% of the sonicated particles have a particle size between a range of 459-712 nm.

According to one embodiment herein, the protein nanoparticles have a particle size in a range of 164-342 nm and the protein nanoparticles have the particle size preferably in a range of 600-1400 nm.

According to one embodiment herein, a mean particle size of the hydrolyzed particles is reduced from 297 nm to 127 nm after ultrasonic treatment or sonication.

According to one embodiment herein, the particle size is reduced by increasing the enzyme concentration up to 4% in all substrate concentration.

According to one embodiment herein, the hydrolysis time of the enzyme nanoparticle is increased from 96 hours to 288 hours to reduce a particle size.

According to one embodiment herein, the FTIR spectroscopy analysis confirms the presence of higher proportion of β-sheet structure in the hydrolyzed and the sonicated nanoparticles.

According to one embodiment herein, the crystallinity index of the hydrolyzed nanoparticles is 37.86%, and the crystallinity index of the sonicated nanoparticles is 36.05%.

According to one embodiment herein, the thermal degradation temperature of the hydrolyzed nanoparticles is 58.6% at 252° C. The thermal degradation temperature of the sonicated nanoparticles is 51.8% at 254° C. The thermal degradation temperature in the hydrolyzed and sonicated samples is 335° C.-330° C. respectively.

According to one embodiment herein, a synthesized protein nanoparticle from waste chicken feathers comprising a substrate concentration of 5 g/L wherein the substrate is waste chicken feathers and an enzyme concentration of 3.6%. The enzyme is savinase. The nanoparticles are enzymatically hydrolyzed nanoparticles, and the nanoparticles are enzymatically hydrolyzed for 243 hours.

According to one embodiment herein, the protein nanoparticles have a semi-spherical shape.

According to one embodiment herein, the protein nanoparticles have a particle size in a range of 164-342 nm and the protein nanoparticles have the particle size preferably in a range of 600-1400 nm.

According to one embodiment herein, the sonicated nanoparticles has a particle size of 297 nm. 68.2% of the sonicated particles have a particle size of less than 100 nm. 25.3% of the sonicated particles have a particle size within a range of 100-120 nm. 1.5% of the sonicated particles have a particle size in the range of 120-140. 5% of the sonicated particles have a particle size between a range of 459-712 nm. A mean particle size of the hydrolyzed particles is 127 nm after ultrasonic treatment or sonication.

According to one embodiment herein, the crystallinity index of the hydrolyzed nanoparticles is 37.86%. The crystallinity index of the sonicated nanoparticles is 36.05%.

According to one embodiment herein, the thermal degradation temperature of the hydrolyzed nanoparticles is 58.6% at 252° C. The thermal degradation temperature of the sonicated nanoparticles is 51.8% at 254° C. The thermal degradation temperature in the hydrolyzed and sonicated samples is 335° C. and 330° C. respectively.

According to one embodiment herein, the steps involved in the synthesis of protein nanoparticles from waste chicken feathers, the steps are: pretreatment of feathers, enzymatic hydrolysis of feather fibers, experimental design to analyze the effects of enzyme concentration, hydrolysis time and substrate concentration and characterization of feather nanoparticles.

According to one embodiment herein, the feathers are first washed in an aqueous solution comprising of 1 g/l of a nonionic detergent and 1% (OWF) of sodium carbonate at liquor to fiber ratio of 40 ml/g for 30 min at 60° C. The feathers are then rinsed thoroughly and dried. Feathers are then Soxhlet extracted with petroleum ether for approximately 12 h (boiling range 40-60° C.) to remove grease. The petroleum ether is evaporated and the feathers are rinsed with distilled water several times before drying at ambient temperature. Cleaned defatted fibers are then separated from the quill and chopped into short pieces before enzymatic treatment.

According to one embodiment herein, feather fibers are incubated with Savinase in 10 ml of borate buffer solution (50 mM, pH=8.5) comprising 6 g/L sodium bisulfite (a reducing agent) as well as 1 g/L sodium dodecyl sulfate (SDS as an anionic surfactant) at 55° C. according to the experimental design. Sodium bisulfite is used to break down the cystine disulfide bonds in combination with the protease to catalyze the hydrolytic cleavage of the protein fiber into smaller polypeptide chains. The reduction of disulfide bonds by means of a suitable redox leads to protein denaturation facilitating the attack of proteases during proteolysis.

Samples are scooped at different processing time and the enzyme in the mixtures is deactivated by adding a solution of acetic acid (1M) to lower the pH of the treatment baths to 4.5 while raising the temperature up to 75° C. for 20 min with an agitation of 300 rpm. Successively, the mixtures are individually centrifuged at 8000 rpm for 5 min to separate the particles from the remaining solution. Each supernatant is then decanted. The particle fractions are repeatedly washed with deionized water and centrifuged at 8000 rpm.

According to one embodiment herein, the effects of three variables, i.e. enzyme concentration (%), hydrolysis time (h) and substrate concentration (g/l), are investigated and optimized using a three-level Box-Behnken Design (BBD). A 15-run BBD, including three replicates at the center point, is used to fit a regression equation which is applied to optimize the process factors affecting the particle size of the hydrolyzed feather. For statistical calculations, the variables are coded +1, 0, and −1 for high, intermediate and low values, respectively.

The mathematical relationship between the response (particle mean size of each suspension) and the independent variables can be presented by a second-order polynomial regression model as given by Eq. (1):

$$Y=\beta_0+\Sigma_{i=1}^3 \beta_i x_i+\Sigma_{i=1}^3 \beta_{ii} x_i^2+\Sigma_{i=1}^2 \Sigma_{j=i+1}^3 \beta_{ij} x_i x_j$$

where Y represents the predicted response, $x_i$ and $x_j$ are the coded values of independent variables, $\beta_0$, $\beta_i$, $\beta_{ii}$, $\beta_{ij}$ are the intercept, linear, quadratic and interaction coefficients, respectively.

The experimental data analysis is performed using Design-Expert software (Version 7.1.5, 2008; Stat-Ease, Minneapolis, Minn.) to yield regression equation and determine the optimum parameter combinations. The statistical significance of the model coefficients are determined by analysis of variance (ANOVA) combined with the application of Fisher's F-test at a probability P value of 0.05. The accuracy of the model is also checked by the coefficient of determination R2 as the measure of goodness of fit of the model. The fitted polynomial equation is then expressed in the form of three-dimensional response surfaces and two-dimensional contour plots to illustrate the relationship between the response and the variables.

The optimal values of the independent parameters are attained by solving the regression equation along with analyzing the response surfaces and contour plots. An additional experiment is subsequently conducted to verify the validity of the statistical experimental strategies.

According to one embodiment herein, based on the statistical strategies, it is found that minimum particle size is achieved by the following conditions: 5 g/L feather and 3.6% enzyme and a hydrolysis time of 243 h. For a further confirmation an experiment is conducted under these predicted optimum conditions. The enzymatic hydrolysis is performed using 5 g/L feather and 3.6% enzyme for 243 h. The obtained particle size corresponds well with the predicted value verified by the accuracy of the response model.

According to one embodiment herein, each centrifuged sample is suspended in distilled water and the particle size distribution is determined by particle size analyzer (Zetasizer, ZEN3600, Malvem Instruments Ltd, Malvern, UK). The sample prepared under the optimum condition is subjected to ultrasonic treatment (Heilscher Ultrasonics UP200S, 200 watts, 24 kHz) for 15 min at 80% amplitude. The possibility of the fragmentation of hydrolyzed fibers into nanoparticles by sonication energy is investigated. The hydrolyzed optimal sample and the collected turbid suspension (sonicated sample) are freeze-dried afterwards for further analysis.

The morphology of the feather particles is evaluated with scanning electron microscope (SEM, Hitachi 54160, Japan), at 15 kV acceleration voltage after gold coating. The Fourier transform infrared (FTIR) analysis is also carried out with Thermo Nicolet Nexus 670 spectrophotometer to study the chemical changes in the wave number range of 4000 to 400 $cm^{-1}$ at a resolution of 4 $cm^{-1}$ using KBr pellets. Besides, the crystallinity of the particles is determined by X-ray diffraction technique which is conducted with Equinox 3000 (INEL, France). Thermo-gravimetric analysis (TGA) and differential scanning calorimetry (DSC) are performed by TGA50 (Shimadzu, Japan) and METTLER TOLEDO (Germany), respectively, at a heating rate of 10° C./min in flowing nitrogen atmosphere.

According to one embodiment herein, the optimum hydrolysis conditions are found to be enzyme concentration 3.6%, the substrate concentration 5 g/l and hydrolysis time 243 h. Scanning electron micrographs indicated fiber fibrillation and degradation as it is progressively converted into particles form. The results of particle size analysis indicated the positive effect of sonication on reducing particles size. Fourier transform infrared spectra shows no remarkable changes in the chemical composition of treated samples.

According to one embodiment herein, protein nanoparticles from waste chicken feathers are produced by enzymatic hydrolysis followed by ultrasonic treatment. The effects of enzyme concentration, hydrolysis time, and substrate concentration on particle mean size are investigated to optimize the best condition in order to attain the smallest particles by a Box-Behnken Design. It is found that minimum particle size is obtained by using 5 g/L feather and 3.6% enzyme at hydrolysis time of 243 h. A validation assay confirms the predictive response value under the optimal conditions.

SEM images illustrate the fiber fibrillation and degradation as the feather proteins are progressively converted into particles form. The results of particle size analysis indicate that the mean size of the hydrolyzed particles declined from 297 nm to 127 nm after ultrasonic treatment. FTIR spectra demonstrates that no significant change in the chemical structure of feather after the applied procedures. Based on the results of X-ray diffraction analysis the enzymatic hydrolysis and ultrasonic treatments have no significant influence on the X-ray pattern, however, the crystallinity index increased owing to the destruction of the amorphous regions. In addition, thermal stability of feather nanoparticles enhanced comparing to the raw feather. The produced nanoparticles have potential for a variety of applications in different fields such as nano-composites and adsorbents.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 3A-3F illustrates the Scanning Electron Microscope (SEM) images of feather samples: (a) untreated fiber at 600×, (b-c) fiber degradation and fibrillation during enzymatic treatment at 1000× and 6000×, (d) hydrolyzed feather at 15000×, (e) hydrolyzed and sonicated feather at 60000×, and (f) feather nanoparticles at 100000×, according to an embodiment herein.

Figure 1:
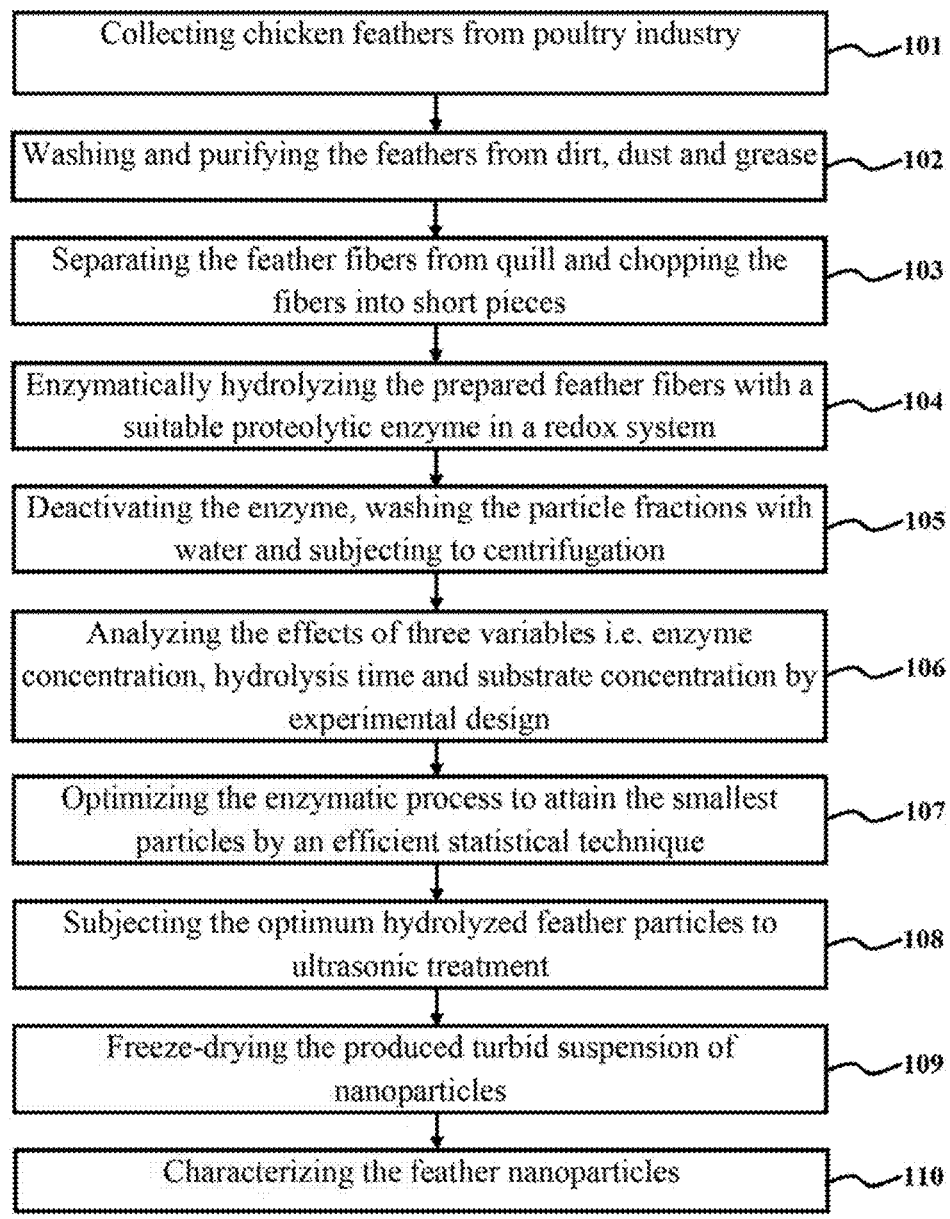
FIG. 1 illustrates a flowchart indicating a method for synthesizing and characterizing the protein nanoparticles synthesized from waste chicken feathers, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide protein nanoparticles synthesized from waste chicken feathers by enzyme hydrolysis followed by ultrasonic treatment. The present invention also examines the influence of enzyme concentration, substrate concentration and hydrolysis time on the particle size of the protein nanoparticles synthesized from waste chicken feather. Further the process of synthesizing the protein nanoparticle from waste chicken feather is optimized by using Response Surface Methodology (RSM). The process of synthesizing protein nanoparticles has milder processing conditions thereby leaving no harmful by products. The protein nanoparticles synthesized from waste chicken feather with enhanced crystallinity and thermal stability.

According to one embodiment herein, a method of synthesizing protein nanoparticles from waste chicken feathers, comprises the following steps of pretreating the plurality of waste chicken feathers, hydrolyzing the plurality of waste chicken feather fibers enzymatically, analyzing the effects of an enzyme concentration, a hydrolysis time and a substrate concentration and synthesizing the feather nanoparticles according to a particle shape, a particle size, crystallinity index and thermal stability characteristics.

According to one embodiment herein, the steps of pretreating the chicken feathers comprises washing the plurality of waste chicken feathers in an aqueous solution for 30 minutes at 60° C. The aqueous solution comprises 1 g/L of a non-ionic detergent and 1 weight % of sodium carbonate at liquid to fiber ratio of 40 ml/g. Further rinsing the chicken feathers and drying. The chicken feathers are subjected to a Soxhert extracting, where the chicken feathers are boiled in the petroleum ether for 12 hours to remove grease to obtain de-fattened feather fibers. The chicken feathers are boiled in petroleum ether at 40-60° C. The petroleum ether is evaporated. The chicken feathers are rinsed with distilled water for a plurality of times. The chicken feathers are dried at room temperature. The de-fattened feather fibers are cleaned. The cleaned and de-fattened feather fibers are separated from quill and the de-fattened fibers are chopped into short pieces.

According to one embodiment herein, the steps of hydrolyzing the chicken feathers enzymatically comprises of incubating the feather fibers with savinase in a 10 ml borate buffer solution at 55° C. The borate buffer solution comprises 6 g/L of a sodium bisulfate and a 1 g/L sodium dodecyl sulfate (SDS). The sodium bisulfate is a reducing agent and the SDS is an anionic surfactant. The hydrolyzed feather fiber samples are scooped out at a plurality of processing intervals, and the plurality of processing intervals have mutually different time periods. The plurality of processing intervals is 3.

According to one embodiment herein, the enzyme savinase is deactivated by adding a solution of an acetic acid (1M). The acetic acid is added to reduce the pH to 4.5. The temperature is increased to 75° C. for 20 min. The enzyme and feather fiber solution is agitated at 300 rpm. The plurality of hydrolyzed feather samples are centrifuged at 8000 rpm for 5 min to separate the particles from residual solution. The supernatants are decanted from particle fraction after centrifugation. The particle fraction is repeatedly washed with deionized water. The particle fraction with deionized water is centrifuged at 8000 rpm; and drying the particle fraction.

According to one embodiment herein, the steps of analyzing the effects of an enzyme concentration, a hydrolysis time and a substrate concentration comprises of acquiring the scooped out feather samples at the plurality of processing intervals. The enzyme concentration, the hydrolysis time and the substrate concentration are estimated in each sample acquired at the plurality of processing intervals. The estimated enzyme concentration, hydrolysis time and substrate concentration are substituted in each sample in a regression equation. The regression equation is fitted in a statistical model represented by a 15 run Box-Behnken Design (BBD) model to obtain an experimental data to optimize the enzyme concentration (%), the hydrolyzing time (h) and the substrate concentration (g/L). The experimental data is analyzed using a Design-Expert Software to yield a regression equation. The optimum parameter combinations of the enzyme concentration, the hydrolysis time and the substrate concentration are determined. The optimal values of the independent parameters of enzyme concentration, hydrolysis time and substrate concentration are obtained by solving the regression equation. The surface response and contour plots for the parameters of enzyme concentration, hydrolysis time and substrate concentration are analyzed. The optimal substrate concentration is found to be 5 g/L feather, the optimal enzyme concentration is found to be 3.6% and the optimal hydrolysis time is found to be 243 hours.

According to one embodiment herein, the steps of synthesizing the feather nanoparticles according to the particle shape, the particle size, crystallinity index and the thermal stability characteristics comprises of suspending the centrifuged particle fraction in distilled water for determining a particle size distribution. The particle size distribution is determined by a particle size analyzer. The centrifuged particles are subjected to ultrasonic treatment for 15 min at 80% amplitude. The morphology of the chicken feather nanoparticles is evaluated with a scanning electronic microscope.

According to one embodiment herein, the nano particles are subjected to a sonication (ultrasonication), a surface morphology analysis, a particle size analysis, a FTIR spectroscopy, a XRD, and a thermal analysis for synthesizing the nano particles according to particle shape, size and thermal stability characteristics.

According to one embodiment herein, the nanoparticles are subjected to the sonication to reduce the particle size from 297 nm to 127 nm after sonication. 68.2% of the sonicated particles have a particle size of less than 100 nm.

25.3% of the sonicated particles have a particle size within a range of 100-120 nm. 1.5% of the sonicated particles have a particle size in the range of 120-140. 5% of the sonicated particles have a particle size between a range of 459-712 nm.

According to one embodiment herein, the protein nanoparticles have a particle size in a range of 164-342 nm and the protein nanoparticles have the particle size preferably in a range of 600-1400 nm.

According to one embodiment herein, a mean particle size of the hydrolyzed particles is reduced from 297 nm to 127 nm after ultrasonic treatment or sonication.

According to one embodiment herein, the particle size is reduced by increasing the enzyme concentration up to 4% in all substrate concentration.

According to one embodiment herein, the hydrolysis time of the enzyme nanoparticle is increased from 96 hours to 288 hours to reduce a particle size.

According to one embodiment herein, the FTIR spectroscopy analysis confirms the presence of higher proportion of β-sheet structure in the hydrolyzed and the sonicated nanoparticles.

According to one embodiment herein, the crystallinity index of the hydrolyzed nanoparticles is 37.86%, and the crystallinity index of the sonicated nanoparticles is 36.05%.

According to one embodiment herein, the thermal degradation temperature of the hydrolyzed nanoparticles is 58.6% at 252° C. The thermal degradation temperature of the sonicated nanoparticles is 51.8% at 254° C. The thermal degradation temperature in the hydrolyzed and sonicated samples is 335° C.-330° C. respectively.

According to one embodiment herein, a synthesized protein nanoparticle from waste chicken feathers comprising a substrate concentration of 5 g/L wherein the substrate is waste chicken feathers and an enzyme concentration of 3.6%. The enzyme is savinase. The nanoparticles are enzymatically hydrolyzed nanoparticles, and the nanoparticles are enzymatically hydrolyzed for 243 hours.

According to one embodiment herein, the protein nanoparticles have a semi-spherical shape.

According to one embodiment herein, the protein nanoparticles have a particle size in a range of 164-342 nm and the protein nanoparticles have the particle size preferably in a range of 600-1400 nm.

According to one embodiment herein, the sonicated nanoparticles have a particle size of 297 nm. 68.2% of the sonicated particles have a particle size of less than 100 nm. 25.3% of the sonicated particles have a particle size within a range of 100-120 nm. 1.5% of the sonicated particles have a particle size in the range of 120-140. 5% of the sonicated particles have a particle size between a range of 459-712 nm. A mean particle size of the hydrolyzed particles is 127 nm after ultrasonic treatment or sonication.

According to one embodiment herein, the crystallinity index of the hydrolyzed nanoparticles is 37.86%. The crystallinity index of the sonicated nanoparticles is 36.05%.

According to one embodiment herein, the thermal degradation temperature of the hydrolyzed nanoparticles is 58.6% at 252° C. The thermal degradation temperature of the sonicated nanoparticles is 51.8% at 254° C. The thermal degradation temperatures in the hydrolyzed and sonicated samples are 335° C. and 330° C. respectively.

FIG. 1 illustrates a flowchart indicating a method for synthesizing and characterizing the protein nanoparticles synthesized from waste chicken feathers, according to an embodiment herein. With respect to FIG. 1, the first step is collecting the chicken feathers from poultry industry (101). The next step is washing and purifying the feathers from dirt, dust and grease (102). Further separating the feather fibers from quill and chopping the fibers into short pieces (103). The next step is enzymatically hydrolyzing the prepared feather fibers with a suitable proteolytic enzyme in a redox system (104). The next step is deactivating the enzyme, washing the particles fractions with water and subjecting to centrifugation (105). Further analyzing the effects of three variables i.e. enzyme concentration, hydrolysis time and substrate concentration by experimental design (106). The next step is optimizing the enzymatic process to attain the smallest particles by an efficient statistical technique (107). Further subjecting the optimum hydrolyzed feather particles to ultrasonic treatment (108). The produced turbid suspension of nanoparticles is subjected to freeze drying (109). The feather nanoparticles are subjected for characterization (110).

Experimental Details

Materials and Methods

Materials:

The experiments were conducted on feathers collected from a slaughterhouse. The proteolytic enzyme was the alkaline serine endoprotease, Savinase 16.0 LEX (EC.3.4.21.14), supplied by Novozymes A/S (Denmark). The nonionic detergent, Diadavin EWN01, was provided by Resin Saveh Co. (Iran). All other chemicals such as sodium carbonate, sodium bisulfite, sodium dodecyl sulfate (SDS), borax, boric acid, and acetic acid was of analytical grade and purchased from Merck Co. (Germany).

Preparation of Feathers:

Feathers were firstly washed in an aqueous solution containing 1 g/l of a nonionic detergent and 1% (OWF) of sodium carbonate at liquor to fiber ratio of 40 ml/g for 30 min at 60° C., then rinsed thoroughly and dried. Feathers were then Soxhlet extracted with petroleum ether for approximately 12 h (boiling range 40-60° C.) to remove grease. The petroleum ether was evaporated and the feathers were rinsed with distilled water several times before drying at ambient temperature. Cleaned defatted fibers were then separated from the quill and chopped into short pieces before enzymatic treatment.

Enzyme Hydrolysis of Feather Fibers:

Feather fibers were incubated with Savinase in 10 ml of borate buffer solution (50 mM, pH=8.5) containing 6 g/l sodium bisulfite (a reducing agent) as well as 1 g/l sodium dodecyl sulfate (SDS as an anionic surfactant) at 55° C. according to the experimental design. Sodium bisulfite was used to break down the cystine disulfide bonds in combination with the protease to catalyze the hydrolytic cleavage of the protein fiber into smaller polypeptide chains. Indeed, the reduction of disulfide bonds by means of a suitable redox leads to protein denaturation facilitating the attack of proteases during proteolysis.

Samples were scooped at different processing time and the enzyme in the mixtures was deactivated by adding a solution of acetic acid (1M) to lower the pH of the treatment baths to 4.5 while raising the temperature up to 75° C. for 20 min with an agitation of 300 rpm. Successively, the mixtures were individually centrifuged at 8000 rpm for 5 min to separate the particles from the remaining solution. Each supernatant was then decanted; the particle fractions were repeatedly washed with deionized water and centrifuged at 8000 rpm.

Experimental Design:

The effects of three variables, i.e. enzyme concentration (%), hydrolysis time (h) and substrate concentration (g/l), were investigated and optimized using a three-level Box-Behnken Design (BBD). Therefore, a 15-run BBD, including three replicates at the center point, was used to fit a regression equation which was applied to optimize the process factors affecting the particle size of the hydrolyzed feather. The factors and their levels are given in Table 1. For statistical calculations, the variables were coded +1, 0, and −1 for high, intermediate and low values, respectively. The Table 1 is shown below:

|  | Levels | | |
|---|---|---|---|
| Independent factors | −1 | 0 | +1 |
| A: enzyme concentration (%) | 2.5 | 3.5 | 4.5 |
| B: hydrolysis time (h) | 96 | 192 | 288 |
| C: substrate concentration (g/l) | 5 | 15 | 25 |

The mathematical relationship between the response (particle mean size of each suspension) and the independent variables can be presented by a second-order polynomial regression model as given by Eq. (1):

$$Y = \beta_0 + \sum_{i=1}^{3} \beta_i x_i + \sum_{i=1}^{3} \beta_{ii} x_i^2 + \sum_{i=1}^{2}\sum_{j=i+1}^{3} \beta_{ij} x_i x_j \quad (1)$$

where Y represents the predicted response, $x_i$ and $x_j$ are the coded values of independent variables, $\beta_0$, $\beta_i$, $\beta_{ii}$, $\beta_{ij}$ are the intercept, linear, quadratic and interaction coefficients, respectively.

The experimental data analysis was performed using Design-Expert software (Version 7.1.5, 2008; Stat-Ease, Minneapolis, Minn.) to yield regression equation and determine the optimum parameter combinations. The statistical significance of the model coefficients were determined by analysis of variance (ANOVA) combined with the application of Fisher's F-test at a probability P value of 0.05. The accuracy of the model was also checked by the coefficient of determination $R^2$ as the measure of goodness of fit of the model. The fitted polynomial equation was then expressed in the form of three-dimensional response surfaces and two-dimensional contour plots to illustrate the relationship between the response and the variables.

The optimal values of the independent parameters were attained by solving the regression equation along with analyzing the response surfaces and contour plots. An additional experiment was subsequently conducted to verify the validity of the statistical experimental strategies.

Characterization of Feather Nanoparticles:

Each centrifuged sample was suspended in distilled water and the particle size distribution was determined by particle size analyzer (Zetasizer, ZEN3600, Malvem Instruments Ltd, Malvem, UK).

The sample prepared under the optimum condition was subjected to ultrasonic treatment (Heilscher Ultrasonics UP200S, 200 watts, 24 kHz) for 15 min at 80% amplitude. The possibility of the fragmentation of hydrolyzed fibers into nanoparticles by sonication energy was investigated. The hydrolyzed optimal sample and the collected turbid suspension (sonicated sample) were freeze-dried afterwards for further analysis.

The morphology of the feather particles was evaluated with scanning electron microscope (SEM, Hitachi S4160, Japan), at 15 kV acceleration voltage after gold coating. The Fourier transform infrared (FTIR) analysis was also carried out with Thermo Nicolet Nexus 670 Spectrophotometer to study the chemical changes in the wave number range of 4000 to 400 cm$^{-1}$ at a resolution of 4 cm$^{-1}$ using KBr pellets.

Besides, the crystallinity of the particles was determined by X-ray diffraction technique which was conducted with Equinox 3000 (INEL, France). Thermo-gravimetric analysis (TGA) and differential scanning calorimetry (DSC) were performed by TGA50 (Shimadzu, Japan) and METTLER TOLEDO (Germany), respectively, at a heating rate of 10° C./min in lowing nitrogen atmosphere.

Results

Model Building and Statistical Analysis:

A three-level three-factor Box-Behnken design is used for optimizing the enzymatic process. The statistical treatment combinations of the independent variables along with the measured and predicted response values, expressed as mean size of the particles, are summarized in Table 2.

The Table 2 illustrates the Experimental design layout and the obtained results of Box-Behnken design with the independent variables where A denotes enzyme concentration, B denotes hydrolysis time, and C denotes substrate concentration.

| Run No. | Independent variables | | | Coded Values | | | Particles mean size (nm) | |
|---|---|---|---|---|---|---|---|---|
| | A | B | C | A | B | C | experimental | predicted |
| 1 | 3.5 | 288 | 5 | 0 | 1 | −1 | 208 | 187 |
| 2 | 3.5 | 192 | 15 | 0 | 0 | 0 | 450 | 464 |
| 3 | 4.5 | 96 | 15 | 1 | −1 | 0 | 457 | 500 |
| 4 | 4.5 | 192 | 25 | 1 | 0 | 1 | 543 | 496 |
| 5 | 3.5 | 192 | 15 | 0 | 0 | 0 | 484 | 464 |
| 6 | 4.5 | 192 | 5 | 1 | 0 | −1 | 381 | 385 |
| 7 | 3.5 | 96 | 5 | 0 | −1 | −1 | 496 | 468 |
| 8 | 2.5 | 192 | 5 | −1 | 0 | −1 | 614 | 637 |
| 9 | 4.5 | 288 | 15 | 1 | 1 | 0 | 219 | 218 |
| 10 | 2.5 | 288 | 15 | −1 | 1 | 0 | 409 | 471 |
| 11 | 2.5 | 192 | 25 | −1 | 0 | 1 | 751 | 749 |
| 12 | 3.5 | 288 | 25 | 0 | 1 | 1 | 338 | 298 |
| 13 | 2.5 | 96 | 15 | −1 | −1 | 0 | 835 | 753 |
| 14 | 3.5 | 96 | 25 | 0 | −1 | 1 | 513 | 580 |
| 15 | 3.5 | 192 | 15 | 0 | 0 | 0 | 437 | 464 |

Effect of Parameters on Particle Size:

The predictive equation is obtained by fitting the experimental data to the BBD model in Eq. (2), which represents an empirical relationship between the response (particle mean size) and the test variables in coded units:

$$Y = 457 - 126.13A - 140.88B + 55.75C + 47AB + 6.25AC + 28.25BC + 103.25A^2 - 80.25B^2 + 12C^2 \quad (2)$$

The statistical significance of the above equation is checked by the F-test, and the ANOVA results for the proposed model are shown in Table 3. The model F-value of 19.55 and value of probability (P value)>F (0.0022) indicate that the model is significant. Besides, the statistically insignificant lack of fit (with P value of 0.1545) reconfirms the validity of the model. Adequate precision of 16.36, which measures the signal to noise ratio, implies an adequate signal (a ratio greater than 4 is desirable). Table 3 is shown below:

| Source | Sum of squares | DF$^a$ | Mean square | F ratio | P value |
|---|---|---|---|---|---|
| Model | 3.917 × 10$^5$ | 9 | 43525.23 | 19.55 | 0.0022 |
| | Coefficient of determination ($R^2$) = 0.9724 | | | | |
| | Adjusted ($R^2$) = 0.9226 | | | | |
| | Predicted ($R^2$) = 0.5981 | | | | |
| | Adeq. Precision = 16.36 | | | | |
| A: enzyme concentration | 1.273 × 10$^5$ | 1 | 1.273 × 10$^5$ | 57.16 | 0.0006 |

-continued

| Source | Sum of squares | DF[a] | Mean square | F ratio | P value |
|---|---|---|---|---|---|
| B: hydrolysis time | $1.588 \times 10^5$ | 1 | $1.588 \times 10^5$ | 71.31 | 0.0004 |
| C: substrate concentration | 24864.50 | 1 | 24864.50 | 11.17 | 0.0205 |
| AB | 8836.00 | 1 | 8836.00 | 3.97 | 0.1030 |
| AC | 156.25 | 1 | 156.25 | 0.070 | 0.8017 |
| BC | 3192.25 | 1 | 3192.25 | 1.43 | 0.2848 |
| $A^2$ | 39362.08 | 1 | 39362.08 | 17.68 | 0.0085 |
| $B^2$ | 23778.69 | 1 | 23778.69 | 10.68 | 0.0222 |
| $C^2$ | 531.69 | 1 | 531.69 | 0.24 | 0.6457 |
| Residual | 11132.25 | 5 | 2226.45 | | |
| Lack of fit | 9954.25 | 3 | 3318.08 | 5.63 | 0.1545 |
| Pure error | 1178.00 | 2 | 589.00 | | |
| Correlation total | $4.029 \times 10^5$ | 14 | | | |

[a]DF = degrees of freedom

To improve the suggested model, the insignificant coefficients (with P value >0.05) are omitted and the final model is modified as follows:

$$Y = 464.38 - 126.13A - 140.88B + 55.75C + 102.33A^2 - 81.17B^2 \quad (3)$$

The ANOVA results after model reduction is given in Table 4. The coefficient of determination ($R^2$) of 0.9408 with an adjusted $R^2$ (0.9079) is in reasonable agreement with the predicted $R^2$ (0.8147). Comparison between the statistical data of Table 3 and 4 shows that the model F ratio, adequate precision and lack of fit have been improved owing to model adjustment. Table 4 is illustrated below:

| Source | Sum of squares | DF | Mean square | F ratio | P value |
|---|---|---|---|---|---|
| Model | $3.790 \times 10^5$ | 5 | 75802.18 | 28.61 | <0.0001 |
| Coefficient of determination ($R^2$) = 0.9408 | | | | | |
| Adjusted ($R^2$) = 0.9079 | | | | | |
| Predicted ($R^2$) = 0.8147 | | | | | |
| Adeq. Precision = 17.38 | | | | | |
| A: enzyme concentration | $1.273 \times 10^5$ | 1 | $1.273 \times 10^5$ | 48.03 | <0.0001 |
| B: hydrolysis time | $1.588 \times 10^5$ | 1 | $1.588 \times 10^5$ | 59.92 | <0.0001 |
| C: substrate concentration | 24864.50 | 1 | 24864.50 | 9.38 | 0.0135 |
| $A^2$ | 38891.54 | 1 | 38891.54 | 14.68 | 0.0040 |
| $B^2$ | 24473.68 | 1 | 24473.68 | 9.24 | 0.0140 |
| Residual | 23848.44 | 9 | 2649.83 | | |
| Lack of fit | 22670.44 | 7 | 3238.63 | 5.50 | 0.1625 |
| Pure error | 1178.00 | 2 | 589.00 | | |
| Correlation total | $4.029 \times 10^5$ | 14 | | | |

As seen in Table 4, all coefficients are significant on the basis of their P value. Nevertheless, the effect of hydrolysis time and enzyme concentration on particles size (P value <0.0001) are higher than substrate concentration.

Figure 2A:
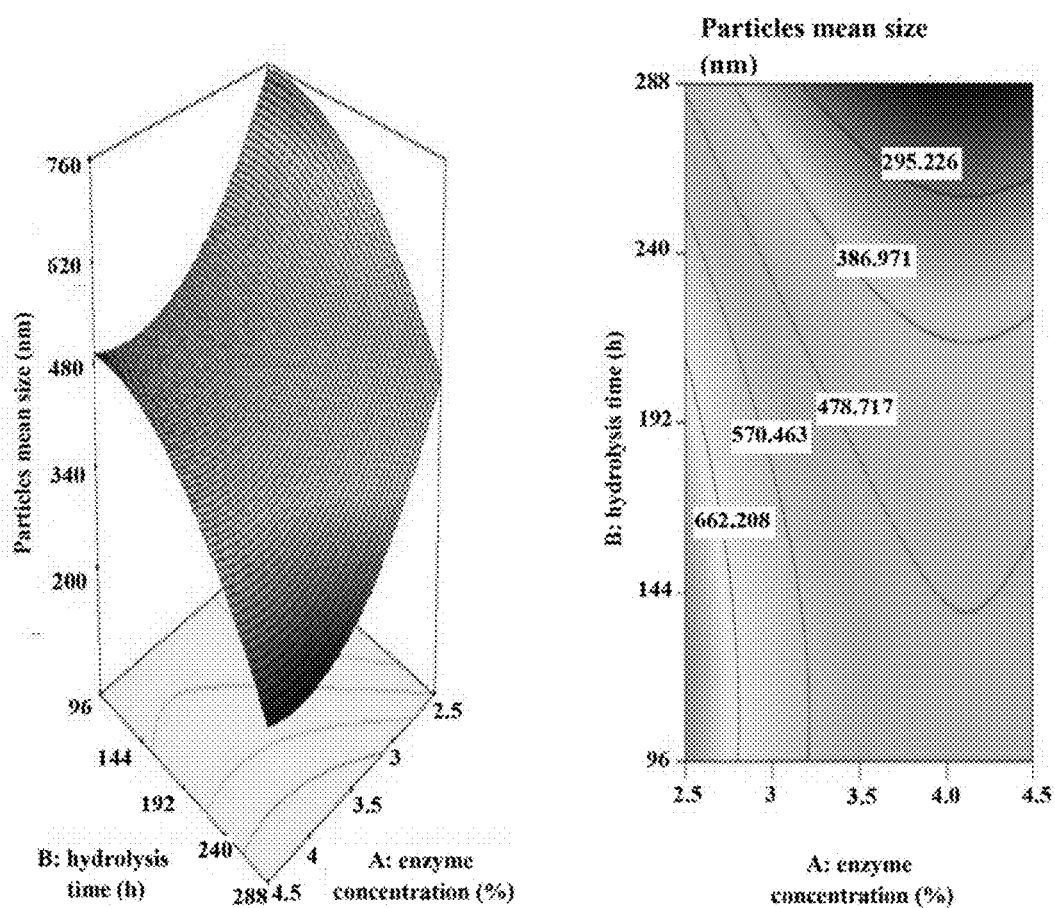
FIG. 2A-2C illustrates the surface response and contour plots of the combined effects of hydrolysis time and enzyme concentration, enzyme and substrate concentration, and hydrolysis time and substrate concentration on particles mean size, according to an embodiment herein.
Figure 2B:
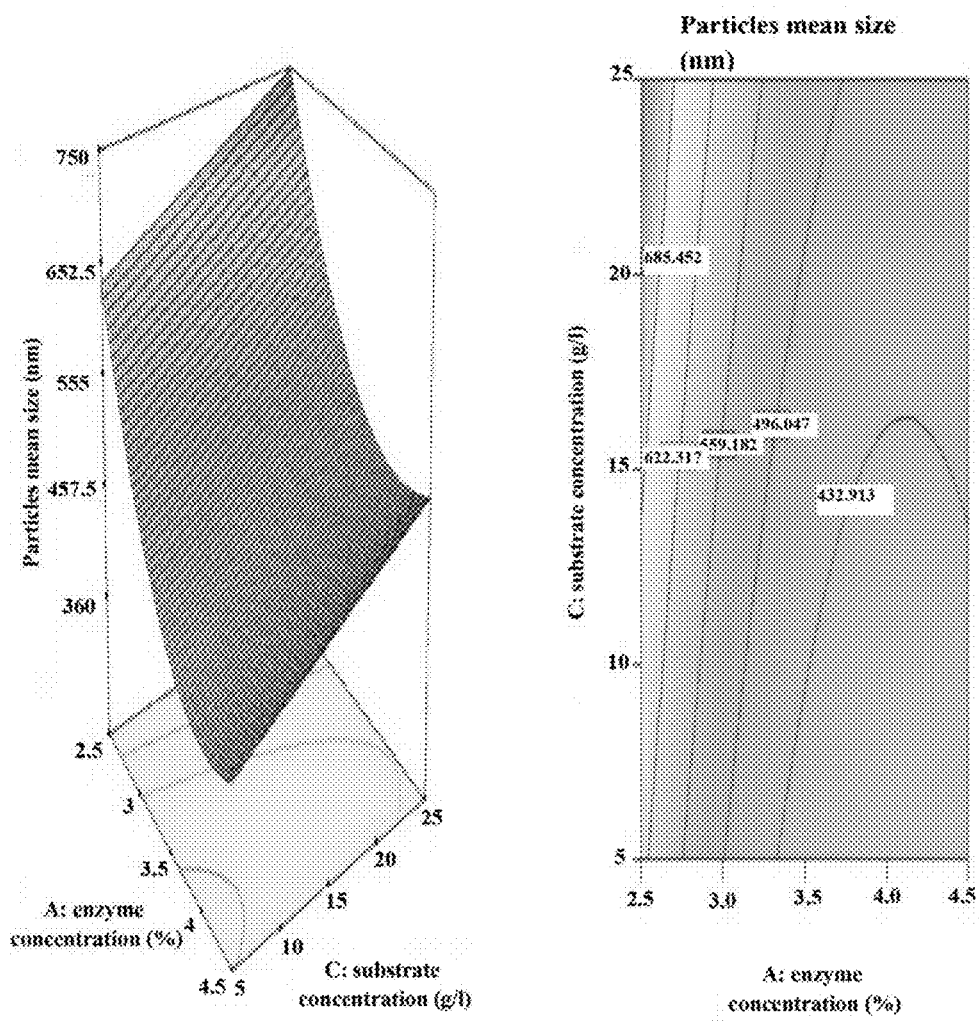
Figure 2C:
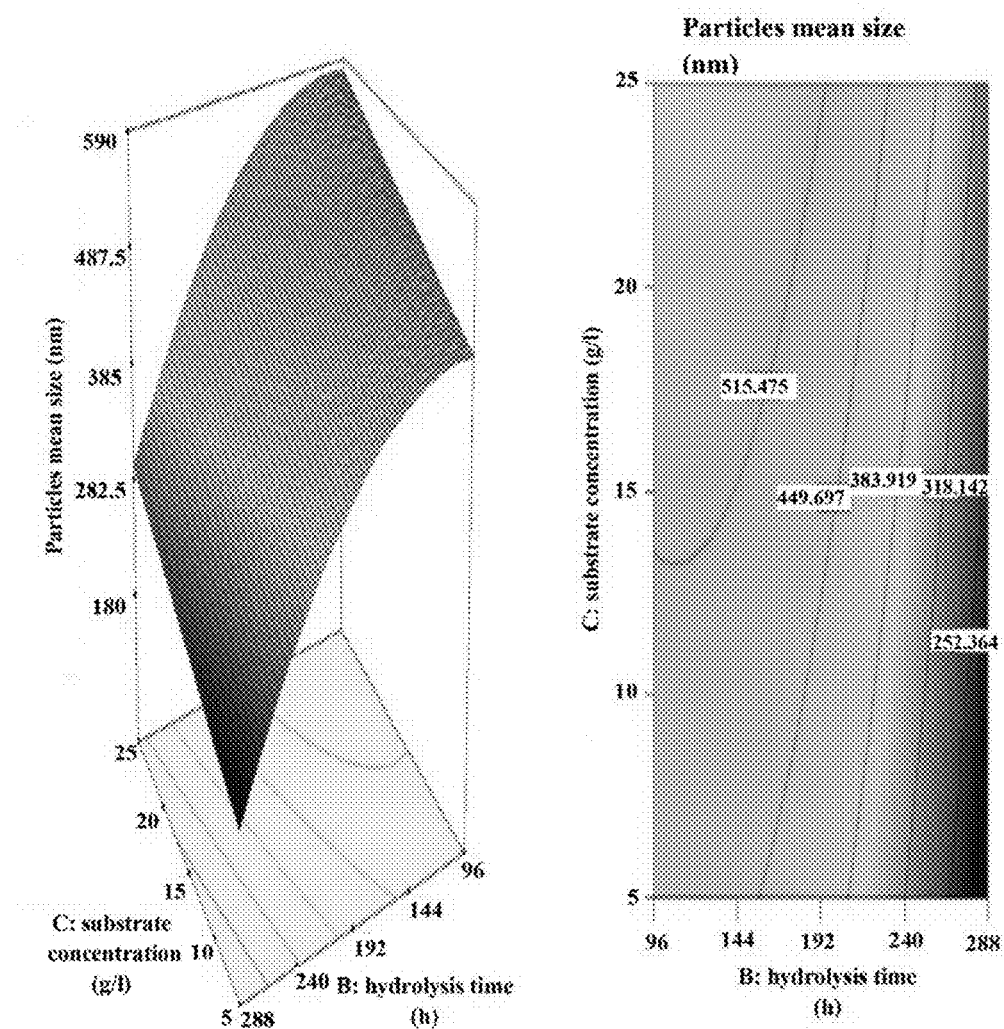

FIG. 2A-2C illustrates the surface response and contour plots of the combined effects of (a) hydrolysis time and enzyme concentration, (b) enzyme and substrate concentration, and (c) hydrolysis time and substrate concentration on particles mean size, according to an embodiment herein.

FIG. 2A illustrates the effects of interaction between hydrolysis time and enzyme concentration on particles size when the other factor (substrate concentration) is at its center point. The plots show that increasing hydrolysis time from 96 h to 288 h leads to a significant fall in particle size in all levels of enzyme concentration. Besides, the quadratic effects of hydrolysis time as well as enzyme concentration are visualized in the response surface, while the former has more significant influence on the particles size validating the results of Table 4.

The surface and contour plots at center point of hydrolysis time (192 h) with varying enzyme and substrate concentration are illustrated in FIG. 2B. It is observed that the decreasing substrate concentration leads to a reduction in particles size especially at high enzyme concentration. Based on the literature, high substrate concentration resulted in low hydrolysis yield due to product/substrate inhibition, enzyme inactivation and a decrease in substrate reactivity with prolonging hydrolysis time. Moreover, the quadratic effect of enzyme concentration over the linear effect of substrate concentration is vividly observed. There is an evident decrease in particles size with increasing enzyme concentration up to approximately 4% in almost all substrate concentrations. In reverse, adding more enzymes causes a slight rise in this response. A constant substrate concentration requires a certain amount of enzyme to reach adsorption saturation for fiber hydrolysis and further increase in enzyme concentration would result in more free protease in the reaction mixture which induces a hindrance for a proteolytic attack. Thus, there is an optimum limit for enzyme concentration to attain the minimum particle size.

FIG. 2C illustrates the effects of hydrolysis time and substrate concentration on particles mean size at center point of enzyme concentration (3.5%). It is observed that there is a decline in particles size with increasing hydrolysis time, particularly at low concentration of substrate. As a consequence, based on the graphical representations of regression equation, minimum particle size is obtained at high level of hydrolysis time, low substrate concentration and optimum amount of enzyme concentration.

Optimization of the Enzymatic Process and Conformation Experiment:

The optimal values of the selected variables are obtained by solving the regression equation using the numerical optimization option of the Design Expert software. It is observed that minimum particle size is achieved by the following conditions: 5 g/l feather and 3.6% enzyme at hydrolysis time of 243 h. The optimized data attained from the proposed model are supported by a further confirmation experiment conducted under the predicted optimum conditions as shown in Table 5. The experimentally obtained particle size (297 nm), corresponding well with the predicted value (303 nm), verified the accuracy of the response model which was adequate for reflecting the expected optimization. Table 5 is illustrated below:

| Variables/Responses | Condition | Lower limit | Upper limit | Solution |
|---|---|---|---|---|
| Enzyme concentration (%) | minimize | 2.5 | 4.5 | 3.6 |
| Hydrolysis time (h) | minimize | 96 | 288 | 243 |
| Substrate concentration (g/l) | In range | 5 | 25 | 5 |
| Particles mean size (nm) | minimize | 208 | 835 | 303 |

Characterization of Feather Nanoparticles:

Feather nanoparticles are produced under the attained optimal conditions followed by ultrasonic treatment. The yield of nanoparticles production (calculated as the percentage of the ratio of the dry mass of nanoparticles to the initial dry mass of feathers) is low (less than 20%). The comparatively low yield of nanoparticles produced by enzymatic hydrolysis and ultrasonic treatment is attributed to the applied enzyme converts a significant amount of feathers into soluble protein fractions.

Three samples including untreated feather fiber, hydrolyzed feather and sonicated feather nanoparticles, are characterized by scanning electron microscopy (SEM), laser diffraction particle size analyzer, Fourier transform infrared (FTIR) spectroscopy, X-ray diffraction (XRD), Thermogravimetric analyzer (TGA), and differential scanning calorimeter (DSC).

Surface Morphology:

Morphological investigation is performed by scanning electron microscope to detect the degree of degradation of feathers upon enzymatic and sonication treatments. FIG. 3A-3F illustrates the Scanning Electron Microscope (SEM) images of feather samples: (a) untreated fiber at 600×, (b-c) fiber degradation and fibrillation during enzymatic treatment at 1000× and 6000×, (d) hydrolyzed feather at 15000×, (e) hydrolyzed and sonicated feather at 60000×, and (f) feather nanoparticles at 100000×, according to an embodiment herein.

FIG. 3A shows the barbs (fibers), with nodes and crotches located longitudinally at regular intervals. FIG. 3B illustrates that the fibers are degraded upon enzymatic treatment and their length and diameter have been reduced. Fibrillation has occurred not only on the surface of the fibers, but at the nodes along the barbs as well. The protease hydrolysis is not only limited to the fiber surface; small protease molecules can easily penetrate into the fiber and hydrolyses the non-keratinous parts leading to complete disintegration of feather structure and fiber fibrillation as well.

FIG. 3C indicates the isolation of the micro-fibrils upon enzymatic treatment. FIG. 3D illustrates surface degradation of these fibrils into particles form is shown in FIG. 3D. As can be seen, the enzymatic attack is not uniform due to the complex structure of feather. Application of ultrasonic energy resulted in more degradation of the hydrolyzed fibers as illustrated in FIG. 3E which was evidenced by formation of a colloidal suspension. FIG. 3F illustrates the semispherical shape of the produced nanoparticles. The sonication causes cavitation and heating. When microscopic cavitation bubbles collapse at the surface of the solid substrate, powerful shock waves as well as enormous shear forces are generated that stimulate effective erosion on the feather surface and help disintegrate possible aggregates having high molecular weight in the solution. The effect of cavitation in heterogeneous systems is hundreds of times more than homogeneous ones.

Figure 4:
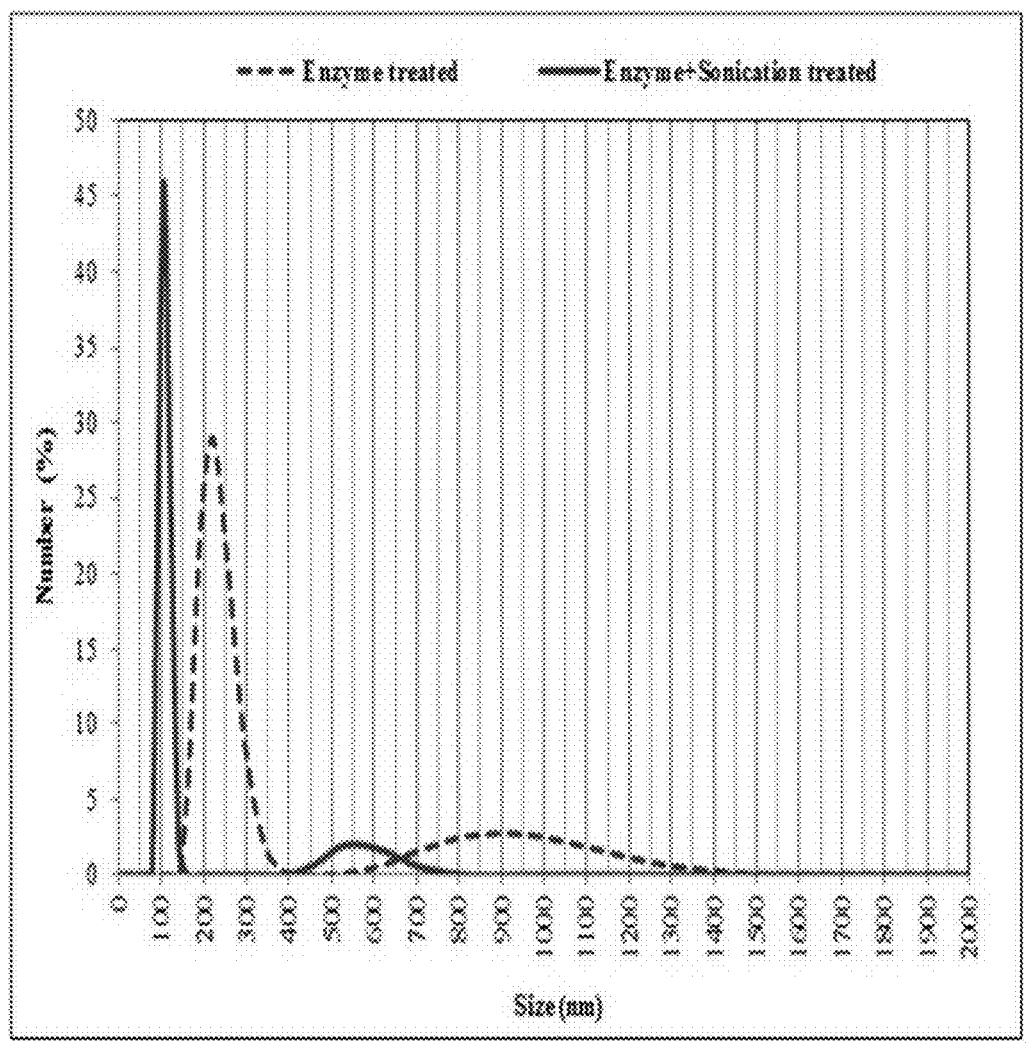
FIG. 4 illustrates a graph indicating the particle size distributions of feather particles by number, according to an embodiment herein.

Particle Size Analysis:

FIG. 4 illustrates a graph indicating the particle size distributions of feather particles by number, according to an embodiment herein.

FIG. 4 illustrates the particle size distributions of the hydrolyzed and sonicated samples. The hydrolyzed particles are mostly in the range of 164-342 nm. Besides, a second broad peak can be seen within 600-1400 nm; however the number of particles lying in this range is much lower than the first major peak. This bimodal distribution confirms the in homogeneous size distribution of the hydrolyzed feather which is consistent with SEM graphs.

Evidently, sonication shifts the particle size distribution towards smaller particles. In fact, large particles of around 900 nm are broken into finer ones with narrower distribution by ultrasonic energy. Furthermore, the mean size of hydrolyzed feather particles has declined from 297 nm to 127 nm after ultrasonic treatment. It is worth noting that 68.2% of the sonicated particles are less than 100 nm, 25.3% within 100-120 nm, 1.5% in the range of 120-140 nm, and only 5% between 459-712 nm.

Figure 5A:
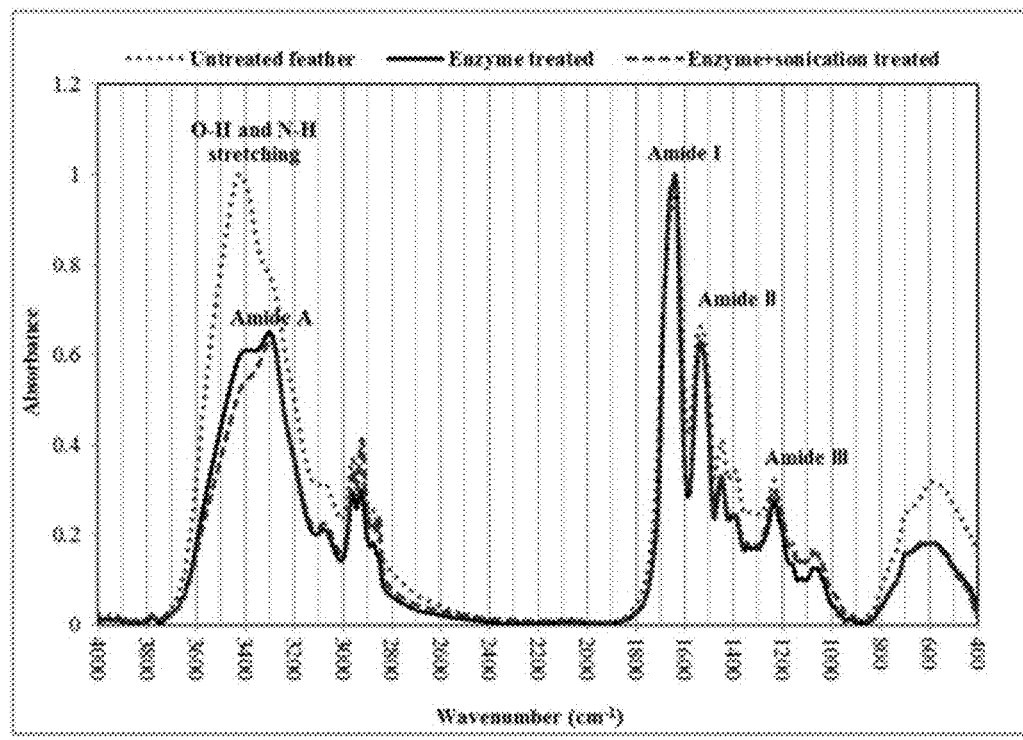
FIG. 5A-5B illustrates graphs indicating FTIR spectra and second-order derivative infrared spectra of untreated feather, enzyme treated, and enzyme+sonication treated feather particles, according to an embodiment herein.
Figure 5B:
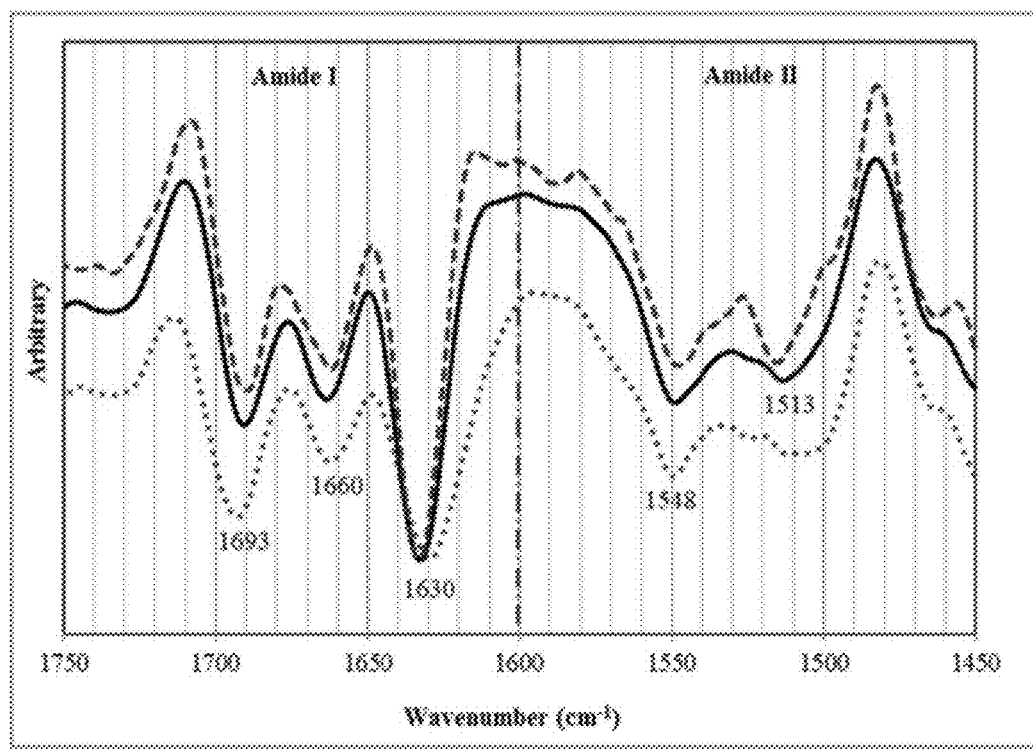

FTIR Spectroscopy:

FIG. 5A-5B illustrates graphs indicating FTIR spectra and second-order derivative infrared spectra of untreated feather, enzyme treated, and enzyme+sonication treated feather particles, according to an embodiment herein.

FIG. 5A illustrates the vibrations in the peptide binds of Amide I, II and III. The FTIR spectra of the samples in FIG. 5A shows characteristic absorption bands attributed mainly to the peptide bonds (CONH). The vibrations in the peptide bonds originate bands known as Amide A, I, II, III. The Amide A band, which falls at 3286 $cm^{-1}$, is connected with the stretching vibration of N—H bonds. The Amide I band is connected mainly with the C=O stretching vibration and it occurs in the range of 1700-1600 $cm^{-1}$, while the Amide II, in the range of 1480-1580 $cm^{-1}$, is related to N—H bending and C—H stretching vibration. The Amide III band, in the range of 1220-1300 $cm^{-1}$, results from in phase combination of C—N stretching and N—H in-plane bending.

The results confirm that there are no significant changes in the chemical structure of feather upon the applied procedures. However, the intensity of absorbing peak in the range of 3200 to 3500 $cm^{-1}$, which is related to the stretching vibration of N—H and O—H bonds, has decreased in the treated samples due to the reduction of hydrogen bonds during enzymatic hydrolysis.

The position and intensity variability of amide bands are associated with the conformational changes in the keratin molecule. Amide I and Amide II bands are known to be sensitive to the secondary structure of proteins. Therefore, these regions were resolved by second-order derivative; it should be noted that the peak positions are inverted in the second-order spectra in FIG. 5B. The absorptions at 1660 $cm^{-1}$ for Amide I and at 1548 $cm^{-1}$ for Amide II indicate the presence of crystalline α-helix structure, whereas the bands of Amide I at 1630 $cm^{-1}$ and Amide II at 1513 $cm^{-1}$ are typically found for β-sheet conformation. Besides, the peak in the 1680-1695 $cm^{-1}$ range illustrates the existence of disordered regions. In the resolved spectra of the treated samples, there is a significant increase in the intensity of the absorption band for Amide I at 1630 $cm^{-1}$ with respect to the 1660 $cm^{-1}$ band coupled with a significant increase of the Amide II component at 1513 $cm^{-1}$ with respect to the 1548 $cm^{-1}$ band. These changes mean that the hydrolyzed and sonicated samples have a higher proportion of β-sheet structure than untreated feather.

Figure 6:
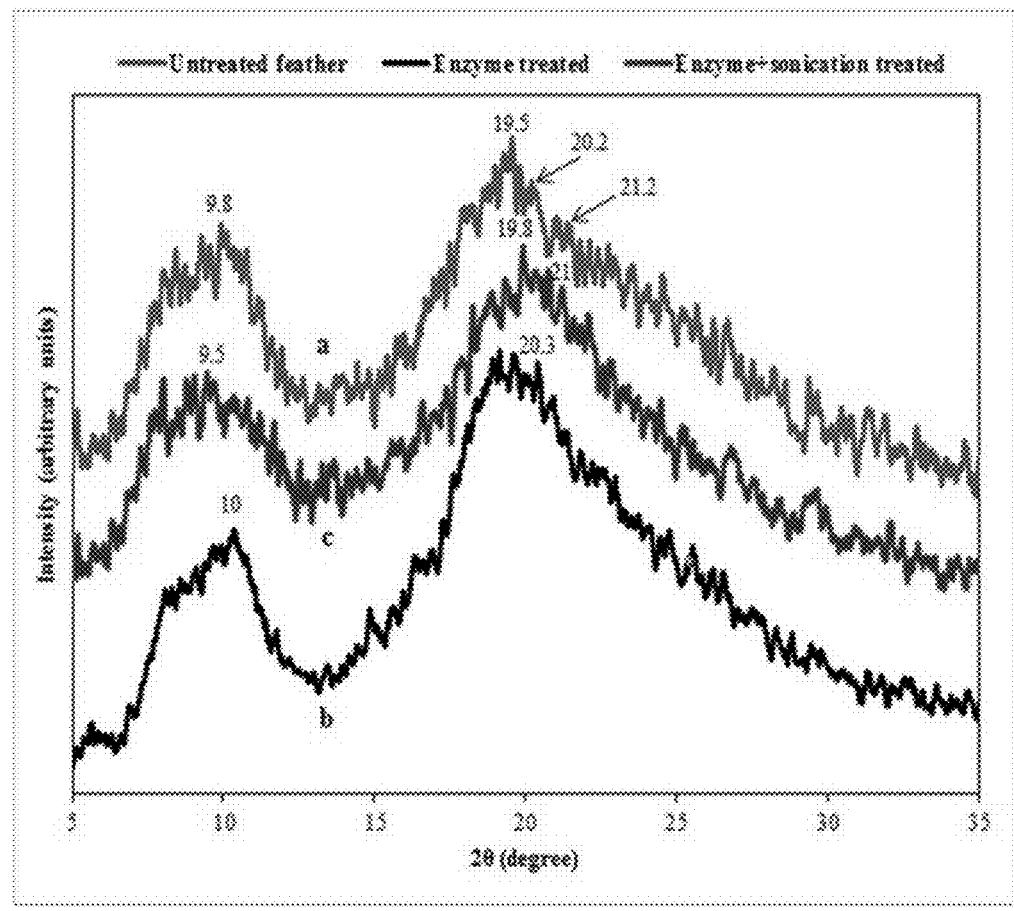
FIG. 6 illustrates graph indicating X-ray diffraction curves of (a) untreated, (b) enzyme treated, and (c) enzyme+ sonication treated feathers, according to an embodiment herein.

X-Ray Diffraction:

Assessment of physical changes in feather is carried out with XRD analysis for determining the crystallinity. FIG. 6 illustrates graph indicating X-ray diffraction curves of (a) untreated, (b) enzyme treated, and (c) enzyme+sonication treated feathers, according to an embodiment herein.

The typical diffraction pattern of α-keratins with a prominent 2θ peak at 20.2° and a minor peak at 9.8°, and the peaks at 2θ of 19.5 and 21.2° indexed as the β-sheet crystalline structure are clearly observed for the raw feather (a) in FIG. 6. As can be seen, there is no change in the X-ray patterns of the hydrolyzed and sonicated samples.

In the case of the sonicated sample (c), the diffraction peaks at 19.8 and 21° has increased, indicating the dominant β-sheet structure in the nanoparticles. However, the higher intensity of the peaks at about 10 and 20.3° in hydrolyzed feather (b) with respect to the sonicated particles suggests the presence of more α-helix crystalline in the former. The degree of crystallinity is determined based on the estimation ratio of the crystalline to amorphous material in each sample. The measured crystallinity index of raw feather, hydrolyzed and sonicated samples are 35.12%, 37.86%, and 36.05%, respectively. The increase in crystallinity is caused by destruction of some amorphous regions in the feather particles. The removal of non-keratinous matrix protein surrounding the crystalline micro-fibrils during enzymatic procedure results in an increase in the proportion of crystallinity.

Figure 7A:
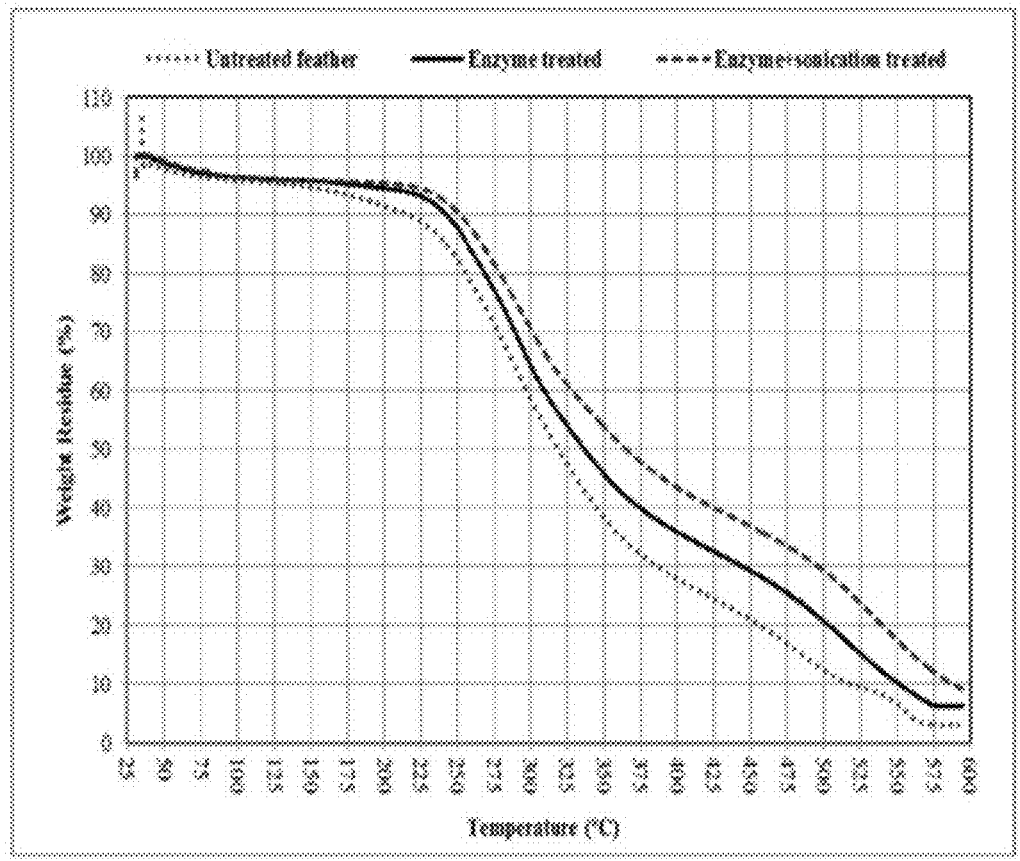
FIG. 7A-7B illustrates graphs indicating the TG and DSC curves of the samples, according to an embodiment herein.
Figure 7B:
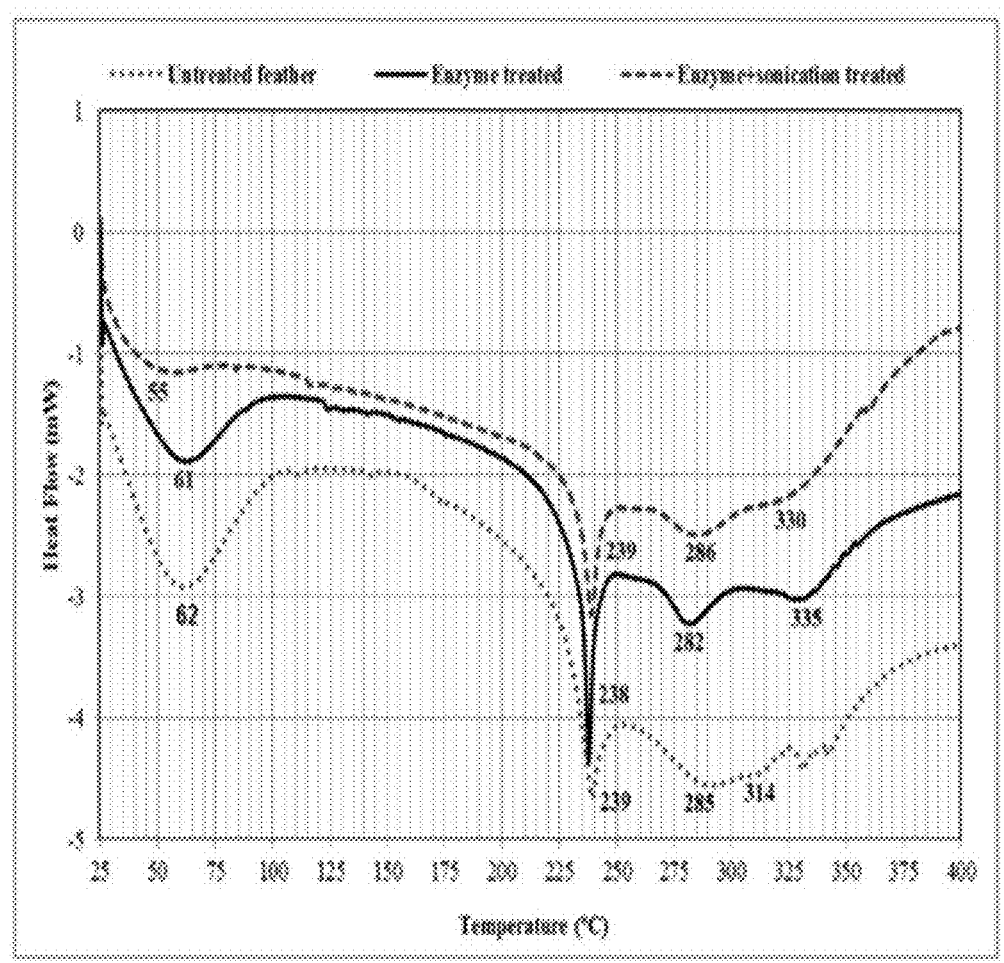

Thermal Analysis:

FIG. 7A-7B illustrates graphs indicating the TG and DSC curves of the samples, according to an embodment herein.

FIGS. 7A and 7B display the TG and DSC curves of the samples, respectively. Two distinct steps of mass loss are observed in thermo-gravimetric graphs. The weight losses in the first and second steps are due to the volatilization of water and the decomposition/denaturation of the protein structure, respectively. The second step is also associated with crystal cleavage, breakdown of cross-links, hydrogen bonds, salt links, peptide bonds, and some changes in the micro fibrillar and matrix regions.

The higher weight remained in the treated samples around 600° C. represents an improvement in the thermal stability of feather particles. This could be attributed to the higher amount of β-sheet crystalline structure in these samples comparing to the untreated feather. The inter-chain interactions in β-sheet conformation are stronger and therefore thermally more stable than intra-chain interactions in α-helix structure. The major weight loss in the temperature range from 200 to 400° C. together with the corresponding thermal degradation temperature ($T_{onset}$) of raw feather, hydrolyzed and sonicated samples are 63.3% (236° C.), 58.6% (252° C.), and 51.8% (254° C.), respectively. The untreated feather lost more weight and degraded at lower temperature in comparison with the treated ones.

The first endothermic peak in DSC curves illustrates the vaporization of absorbed water in the samples, which is consistent with the first weight loss in TG curves. The peak temperature of 62° C. in untreated feather declines to 61° C. and 55° C. in hydrolyzed and sonicated samples, respectively. This implies that the water maintaining abilities of the feather particles changes after enzymatic hydrolysis and ultrasonic treatment. The energy required for removing water from the samples reduces which is related to the increase in crystallinity. The peak is transferred from high temperature to low temperature because of the changes in the glass transition temperature of the particles. The absorbed heat for the glass transition reduced with decreasing particle size and destroying amorphous regions.

The second endothermic peak around 230-240° C. corresponds to the thermal denaturation of α-helical crystallites in the intermediate filaments protein of feather keratin. The temperature of this peak shows no significant change after enzymatic and ultrasonic treatments. Further there is a decrease in the underlying area in sonicated sample with respect to hydrolyzed feather. This also illustrates the presence of the lesser α-helix content in the former, which is consistent with the results of XRD analysis.

The third endothermic peak about 285° C. is ascribed to the melting/decomposition of keratin associated proteins comprising highly cross-linked inter-macrofibrillar matrix keratins. The higher degradation temperature ($T_{onset}$) in the hydrolyzed and sonicated samples (335° C. and 330° C., respectively) in comparison to the raw feather (314° C.) shows their higher thermal stability because of their higher content of crystalline β-sheet structure. The observations correspond to the thermo-gravimetric analysis.

Feather nanoparticles are produced by enzymatic hydrolysis followed by ultrasonic treatment. The effects of enzyme concentration, hydrolysis time, and substrate concentration on particle mean size are investigated to optimize the best condition in order to attain the smallest particles by a Box-Behnken Design. It is found that minimum particle size is obtained by using 5 g/l feather and 3.6% enzyme at hydrolysis time of 243 h. A validation assay confirmed the predictive response value under the optimal conditions.

SEM images confirm that the fiber fibrillation and degradation as it is progressively converted into particles form. The result of particle size analysis indicates that the mean size of the hydrolyzed particles declined from 297 nm to 127 nm after ultrasonic treatment. The FTIR spectra demonstrate no significant changes in the chemical structure of feather after the applied procedures. Based on the results of X-ray diffraction analysis, enzymatic hydrolysis and ultrasonic treatment has no significant influence on the X-ray pattern, however, the crystallinity index increased owing to the destruction of the amorphous regions. In addition, thermal stability of feather nanoparticles enhanced comparing to the raw feather. The produced nanoparticles have promising potential for a variety of applications in different fields such as nano-composites and adsorbents.

According to one embodiment herein, the protein nanoparticles synthesized from waste chicken feathers by enzyme hydrolysis followed by ultrasonic treatment is a green process. Further through this method keratin can also be extracted from this abundant protein source apart from producing high value added nanoparticles.

According to one embodiment herein, the protein nanoparticles synthesized from waste chicken feathers are hydrophobic and water insoluble in comparison with other soluble protein nanoparticles which is helpful in application requires hydrophobic protein nanoparticles such as oil adsorbents.

According to one embodiment herein, the produced nanoparticles have potential for a variety of applications in different fields comprising reinforcement in various kinds of polymeric composites, animal feed ingredient, insulation and filtration material, sorbent of hazardous and toxic compounds and films and coatings. Further the light weight of the produced protein nanoparticles produced from waste chicken feathers combined with their heat insulating capability makes the nanoparticles preferable for applications comprising outdoor clothing and blankets.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method of producing feather nanoparticles from waste chicken feathers, the method comprising steps of:
pretreating a plurality of waste chicken feathers;
hydrolyzing a plurality of waste chicken feather fibers enzymatically;
analyzing effects of an enzyme concentration, a hydrolysis time and a substrate concentration on particle size; and
producing feather nanoparticles according to a particle shape, a particle size, crystallinity index and thermal stability characteristics, and wherein the steps of producing the feather nanoparticles comprises:
suspending a centrifuged particle fraction in distilled water for determining a particle size distribution, and wherein the particle size distribution is determined by a particle size analyzer;
subjecting centrifuged particles to ultrasonic treatment for 15 min at 80% amplitude; and
characterizing physicochemical properties of the produced feather nanoparticles.

2. The method according to claim 1, wherein the steps of pretreating the chicken feathers comprises:
washing the plurality of waste chicken feathers in an aqueous solution for 30 minutes at 60° C., and wherein the aqueous solution comprises 1 g/L of a non-ionic detergent and 1% of sodium carbonate at liquid to fiber ratio of 40 ml/g;
rinsing the chicken feathers and drying;
Soxhlet extracting the chicken feathers by boiling the chicken feathers in petroleum ether for 12 hours to remove grease to obtain de-fattened feather fibers, and wherein the chicken feathers are boiled in petroleum ether at 40-60° C.;
evaporating the petroleum ether;
rinsing the chicken feathers with distilled water for a plurality of times;
drying the chicken feathers at room temperature;
cleaning the de-fattened feather fibers;
separating the cleaned and de-fattened feather fibers from quill; and
chopping the de-fattened fibers into short pieces.

3. The method according to claim 1, wherein the steps of hydrolyzing the chicken feathers enzymatically comprises:
incubating a predetermined amount of feather fibers with a protein hydrolyzing enzyme in a 10 ml borate buffer solution at 55° C., and wherein the borate buffer solution comprises 6 g/L of a sodium bisulfate and a 1 g/L sodium dodecyl sulfate (SDS), and wherein the sodium bisulfate is a reducing agent and wherein the SDS is an anionic surfactant, and wherein the predetermined amount of the feather fibers is selected from the group consisting of 5 g/L, 15 g/L and 25 g/L;
scooping out the hydrolyzed feather fiber samples at a plurality of processing intervals, and wherein the plurality of processing intervals have mutually different time periods, and wherein the plurality of processing intervals is 3;
deactivating the protein hydrolyzing enzyme by adding a solution of an acetic acid (1M), and wherein the acetic is added to reduce the pH to 4.5, and wherein the temperature is increased to 75° C. for 20 min, and wherein the enzyme and feather fiber solution is agitated at 300 rpm;
centrifuging the plurality of hydrolyzed feather samples at 8000 rpm for 5 min to separate the particles from residual solution;
decanting supernatants from particle fraction after centrifugation;
washing the particle fraction repeatedly with deionized water;
centrifuging the particle fraction with deionized water at 8000 rpm; and
drying the particle fraction.

4. The method according to claim 1, wherein the steps of analyzing the effects of an enzyme concentration, a hydrolysis time and a substrate concentration comprises:
acquiring feather samples at a plurality of processing intervals;
substituting the enzyme concentration, hydrolysis time and substrate concentration in each sample in a regression equation;
fitting the regression equation in a statistical model represented by a Box-Behnken Design (BBD) model to obtain an experimental data to optimize the enzyme concentration (%), the hydrolyzing time (h) and the substrate concentration (g/L);
analyzing the experimental data using a Design-Expert Software to yield a regression equation;
determining the optimum parameter combinations of the enzyme concentration, the hydrolysis time and the substrate concentration;
obtaining the optimal values of the independent parameters of enzyme concentration, hydrolysis time and substrate concentration by solving the regression equation; and
analyzing a surface response and contour plots for the parameters of enzyme concentration, hydrolysis time and substrate concentration;
wherein the optimal substrate concentration is 5 g/L feather, and wherein the optimal enzyme concentration is 3.6% and wherein the optimal hydrolysis time is 243 hours.

5. The method according to claim 1, wherein the produced nanoparticles are characterized with a surface morphology analysis (SEM), a particle size analysis (DLS), a FTIR spectroscopy, a XRD, and a thermal analysis (TGA and DCS).

6. The method according to claim 5, wherein the nanoparticles are subjected to sonication to reduce the particle size from 297 nm to 127 nm after sonication, and wherein 68.2% of the sonicated particles has a particle size of less than 100 nm, and wherein 25.3% of the sonicated particles has a particles size within a range of 100-120 nm, and wherein the 1.5% of the sonicated particles has a particle size in the range of 120-140, and wherein the 5% of the sonicated particles has a particle size between a range of 459-712 nm.

7. The method according to claim 1, wherein a mean particle size of the hydrolyzed particles is reduced from 297 nm to 127 nm after ultrasonic treatment, and wherein the ultrasonic treatment is sonication.

8. The method according to claim 1, wherein the particle size is reduced by increasing the enzyme concentration up to 4% in a plurality of substrate concentration.

9. The method according to claim 1, wherein the hydrolysis time of the enzyme is increased from 96 hours to 288 hours to reduce a particle size of the feather protein nanoparticles.

10. The method according to claim 5, wherein the FTIR spectroscopy analysis confirms the presence of higher proportions of β-sheet structure in the hydrolyzed and the sonicated nanoparticles.

11. The method according to claim 5, wherein a crystallinity index of hydrolyzed nanoparticles is 37.86%, and wherein a crystallinity index of sonicated nanoparticles is 36.05%.

12. The method according to claim 5, wherein a thermal degradation temperature of the hydrolyzed nanoparticles is 58.6% at 252° C., and wherein the thermal degradation temperature of the sonicated nanoparticles is 51.8% at 254° C., and wherein the thermal degradation temperature in the hydrolyzed and sonicated samples are 335° C.-330° C. respectively.

* * * * *